United States Patent
Yamamoto (10) Patent No.: US 9,186,281 B2
(45) Date of Patent: Nov. 17, 2015

(54) WEB JOINT APPARATUS AND WEB JOINT METHOD

(75) Inventor: Hiroki Yamamoto, Kagawa (JP)

(73) Assignee: UNICHARM CORPORATION, Ehime (JP)

( * ) Notice: Subject to any disclaimer, the term of this patent is extended or adjusted under 35 U.S.C. 154(b) by 957 days.

(21) Appl. No.: 13/383,638

(22) PCT Filed: Jul. 30, 2010

(86) PCT No.: PCT/JP2010/062945
§ 371 (c)(1),
(2), (4) Date: Jan. 31, 2012

(87) PCT Pub. No.: WO2011/013823
PCT Pub. Date: Feb. 3, 2011

(65) Prior Publication Data
US 2012/0184424 A1   Jul. 19, 2012

(30) Foreign Application Priority Data

Jul. 31, 2009   (JP) .................................. 2009-180201

(51) Int. Cl.
*B31F 1/00* (2006.01)
*A61F 13/15* (2006.01)
(Continued)

(52) U.S. Cl.
CPC ..... *A61F 13/15804* (2013.01); *A61F 13/15739* (2013.01); *B29C 65/086* (2013.01);
(Continued)

(58) Field of Classification Search
CPC ............ B29L 2031/4878; A61F 13/15; A61F 13/5739; A61F 13/158041; B29C 65/00; B29C 65/02; B29C 65/08; B29C 65/083; B29C 65/086; B29C 66/00; B29C 66/01; B29C 66/05; B29C 66/10; B29C 66/11; B29C 66/112; B29C 66/11122; B29C 66/40; B29C 66/41; B29C 66/43; B29C 66/431; B29C 66/4312; B29C 66/43129; B29C 66/433
USPC ......... 156/200, 201, 204, 227, 229, 250, 269, 156/443, 459, 461, 464, 465, 468, 494, 156/496; 493/416, 436, 438, 439, 440, 442, 493/443, 446
See application file for complete search history.

(56) References Cited

U.S. PATENT DOCUMENTS 5,217,739 A * 6/1993 Stein et al. .................. 426/496
6,098,557 A * 8/2000 Couillard et al. ........ 112/475.06
(Continued)

FOREIGN PATENT DOCUMENTS

EP   1609582   12/2005
EP   1719605   11/2006
(Continued)

OTHER PUBLICATIONS

Supplementary European Search Report mailed May 28, 2013 for counterpart EP application No. 10804569.1.
(Continued)

*Primary Examiner* — Andrew M Tecco
*Assistant Examiner* — Joshua Kotis
(74) *Attorney, Agent, or Firm* — Hauptman Ham, LLP (57) ABSTRACT

A web joint apparatus is configured to join a pair of webs for absorbent article folded in the cross direction CD with reference to a folding line. The web joint apparatus includes: an ultrasonic horn configured to join the paired waistline portions; an anvil facing the ultrasonic horn and configured to pinch the intermediate web between the anvil and the ultrasonic horn; and a crotch hold bar configured to hold the intermediate web while stretching the intermediate web in a direction in which the crotch portions get away from the waistline portions, when the intermediate web are joined by the ultrasonic horn and the anvil.

8 Claims, 7 Drawing Sheets

(51) Int. Cl.
   *B29C 65/08* (2006.01)
   *B29C 65/00* (2006.01)
   *B29L 31/48* (2006.01)

(52) U.S. Cl.
   CPC ............ *B29C66/1122* (2013.01); *B29C 66/21* (2013.01); *B29C 66/223* (2013.01); *B29C 66/4312* (2013.01); *B29C 66/43129* (2013.01); *B29C 66/81427* (2013.01); *B29C 66/81433* (2013.01); *B29C 66/83433* (2013.01); *B29C 66/83511* (2013.01); *B29C 66/433* (2013.01); *B29C 66/7294* (2013.01); *B29C 2793/0081* (2013.01); *B29L 2031/4878* (2013.01)

(56) References Cited

U.S. PATENT DOCUMENTS

| | | | |
|---|---|---|---|
| 6,913,664 B2 | 7/2005 | Umebayashi et al. | |
| 6,926,654 B2 | 8/2005 | Yamamoto et al. | |
| 7,060,142 B2 | 6/2006 | Yamamoto | |
| 7,144,357 B2 * | 12/2006 | Yamamoto et al. | 493/34 |
| 7,195,586 B2 * | 3/2007 | Yamamoto et al. | 493/429 |
| 7,632,366 B2 * | 12/2009 | Shimizu et al. | 156/64 |
| 7,887,652 B2 | 2/2011 | Yamamoto | |
| 8,074,693 B2 | 12/2011 | Yamamoto et al. | |
| 8,257,535 B2 * | 9/2012 | Yamamoto | 156/204 |
| 8,273,003 B2 * | 9/2012 | Umebayashi et al. | 493/417 |
| 2007/0142194 A1 * | 6/2007 | Coenen et al. | 493/405 |
| 2010/0050411 A1 | 3/2010 | Yamamoto | |
| 2010/0116409 A1 * | 5/2010 | Yamamoto | 156/73.1 |
| 2010/0179042 A1 | 7/2010 | Yamamoto | |

FOREIGN PATENT DOCUMENTS

| | | | |
|---|---|---|---|
| GB | 2257652 | | 1/1993 |
| JP | 2003038566 A | | 2/2003 |
| JP | 2004298413 A | | 10/2004 |
| JP | 2005046246 A | | 2/2005 |
| JP | 2008-174328 | | 7/2008 |
| JP | 2008-174328 A | | 7/2008 |
| JP | 2008174328 A | * | 7/2008 |
| JP | 2010227545 A | | 10/2010 |
| WO | 2008/126748 | | 10/2008 |
| WO | 2010024373 A1 | | 3/2010 |
| WO | 2010/047303 | | 4/2010 |

OTHER PUBLICATIONS

Notice of Grounds for Rejection mailed Jun. 4, 2013 for counterpart JP application No. 2009-180201.

First Notification of Reasons for Refusal mailed May 30, 2013 for counterpart CN application No. 201080033966.5.

International Search Report and Written Opinion for PCT/JP2010/062945 dated Nov. 2, 2010.

Office Action mailed Apr. 22, 2015, corresponding to Taiwanese patent application No. 099125435.

* cited by examiner

WEB JOINT APPARATUS AND WEB JOINT METHOD

RELATED APPLICATIONS

The present application is a National Phase of International Application Number PCT/JP2010/062945, filed Jul. 30, 2010 and claims priority from Japanese Application Number 2009-180201, filed Jul. 31, 2009.

TECHNICAL FIELD

The present invention relates to a web joint apparatus and a web joint method for joining a pair of waistline portions when a web for an absorbent article including waistline portions and a crotch portion is folded in a cross direction with reference to a folding line parallel with the machine direction on the crotch portion.

BACKGROUND ART

An absorbent article such as a pants-type disposable diaper and the like generally includes such members as waistline portions for the wearer's waistline (specifically, a front waistline portion and a back waistline portion), a crotch portion for the wearer's crotch, and an absorber which absorbs excretion discharged from the wearer. The pants-type diaper is provided with leg-surrounding portions where openings for inserting wearer's legs are formed. Each of the leg-surrounding portions is provided with a leg gather formed with a string-like rubber to fit the leg-surrounding portion to the wearer.

In a manufacturing process of such a pants-type diaper, a web including a continuum of the members described above is conveyed using conveyor belts and the like. In a web folding step, a web is folded into two in the cross direction CD orthogonal to the machine direction MD so that a continuum of front waistline portions and a continuum of back waistline portions can be overlaid one another, while the web provided with leg-surrounding portions is being conveyed in the machine direction MD, that is, in a flow direction of the manufacturing process (Patent Document 1, for example).

Next, in a web joining step, the front waistline portions are joined to the back waistline portions at a predetermined intervals by using a joint apparatus provided with a ultrasonic horn and an anvil roll while the web folded in two are continuously being conveyed in the machine direction (Patent Document 2, for example). Then, in a cutting step, the web is cut into individual pants-type diapers by using a cutting apparatus provided with a cutting blade.

Since leg gathers are provided at the leg-surrounding portions of the web folded into two, the vicinity of the leg-surrounding portions of the web is likely to contract in the cross direction. For this reason, when the doubled web is joined in the joining step with the vicinity of the leg-surrounding portion contracted in the cross section, a crease is likely to occur at a joint portion of the front waistline portion and the back waistline portion, thereby causing a problem of manufacture defects of the absorbent article.

In the joining step, the web is conveyed along outer peripheral surface of the anvil rolls. Also, since an absorber is provided to the crotch portion of the web, the crotch portion is heavier in weight than the waistline portions. Therefore, the crotch portion of the web is likely to float off from the anvil rolls when the crotch portion contracts toward the waistline portions due to contraction of the leg gathers.

As a result, when the web is conveyed along the outer peripheral of the anvil roll, the crotch portion may curl up due to a centrifugal force in a direction in which the crotch portion gets away from the anvil roll, that is, in the normal direction of the anvil roll. At this time, the curled crotch portion may touch the ultrasonic horn or may be clogged in a gap between the ultrasonic horn and the anvil roll, whereby causing manufacture defect of the absorbent article.

PRIOR ART DOCUMENT

Patent Document

Patent Document 1: Japanese patent application publication No. 2005-46246 (Pages 6 and 7 and FIG. 3)
Patent Document 2: Japanese patent application publication No. 2004-298413 (Pages 9 and 10 and FIG. 5 and FIG. 6)

SUMMARY OF INVENTION

A web joint apparatus according to first aspect is configured to convey a web for an absorbent article folded into two in a cross direction orthogonal to the machine direction with reference to a folding line parallel with the machine direction on a crotch portion. The absorbent article includes: paired waistline portions which are continuous in the machine direction along a flow direction of a manufacturing process for an absorbent article; and crotch portions which are discontinuous in the machine direction and located between the paired waistline portions. The web joint apparatus includes: a joint mechanism configured to join the paired waistline portions; an anvil mechanism facing the joint mechanism and configured to join the web between the anvil mechanism and the joint mechanism; and a hold mechanism configured to hold the web while stretching the web in a direction in which the crotch portions get away from the waistline portions, when the paired waistline portions are joined by the joint mechanism and the anvil mechanism

DESCRIPTION OF EMBODIMENTS

Next, embodiments of a web joint apparatus and a web joint method according to the present invention are described referring to the accompanying drawings. In the description of drawings hereinafter, same or similar signs are assigned to same or similar members. Note that the drawings are schematic and ratios of dimensions and the like are different from actual ones.

Therefore, specific dimensions and the like should be determined referring to the description given hereinafter.

Moreover, the drawings also include portions having different dimensional relationships and ratios from each other.

Figure 1:
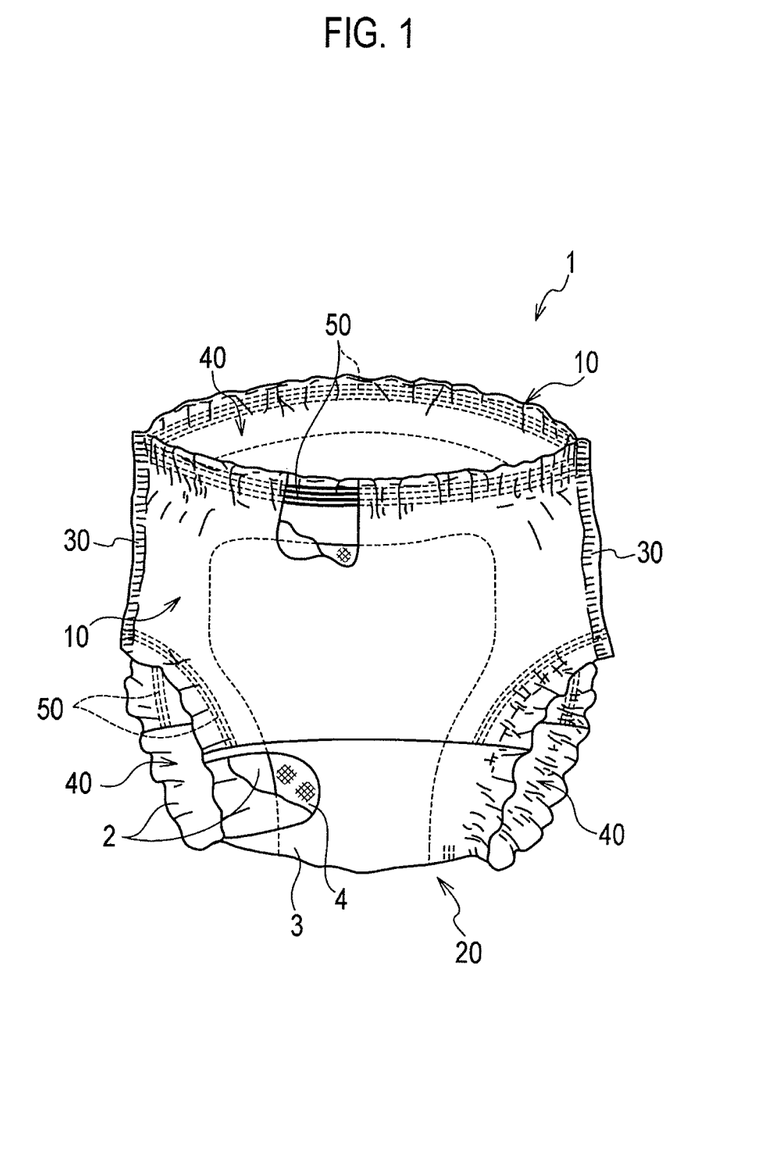
FIG. 1 is a perspective view showing an absorbent article 1 according to this embodiment.

First, with reference to the drawings, description will be provided for a configuration of an absorbent article 1 manufactured by a web joint apparatus and a web joint method according to the present invention. FIG. 1 is a perspective view showing the absorbent article 1 according to this embodiment.

According to this embodiment, the absorbent article 1 is a disposable pants-type diaper. As shown in FIG. 1, the absorbent article 1 mainly comprises a topsheet 2, a backsheet 3 and an absorber 4.

The topsheet 2 is provided at an innermost portion of the absorbent article 1 in contact with wear's skin. The topsheet 2 is a liquid permeable sheet made of a nonwoven fabric or a perforated plastic film, or the like. The backsheet 3 is provided at an outermost portion (on a side away from the wearer) of the absorbent article 1. The backsheet 3 is a liquid permeable sheet or the like. The absorber 4 is provided between the topsheet 2 and the backsheet 3 so as to absorb excretion discharged from the wearer. The absorber 4 is made of a mixture of ground pulp and superabsorbent polymer particles, and the like.

Such absorbent article 1 includes a pair of waistline portions 10 (a front waistline portion and a back waistline portion) to be fitted to the wearer's waistline and a crotch portion 20 to be fitted to the wearer's crotch. The waistline portions 10 are joined together on sides of the wearer's waistline by a joint portion 30.

The absorbent article 1 is provided with multiple openings 40 (a waistline opening portion and leg-surrounding opening portions). A gather 50 formed using a string-like rubber is provided around an entire peripheral edge of each of the openings 40.

Figure 2:
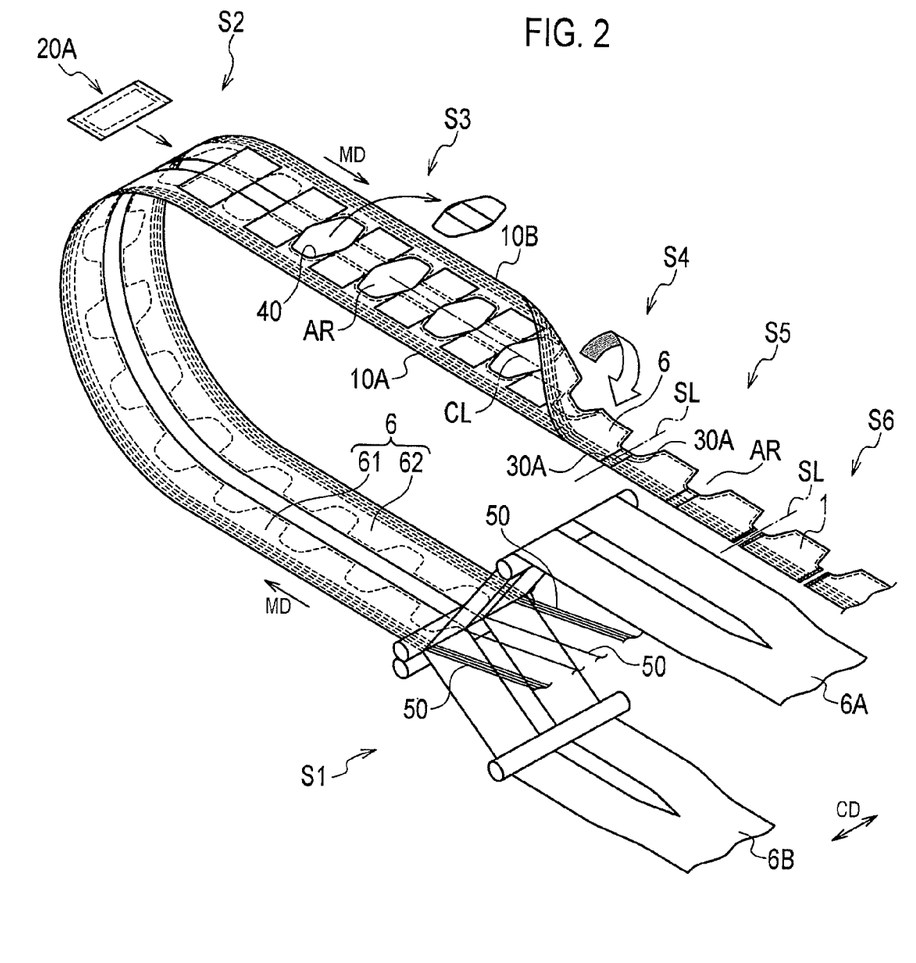
FIG. 2 is a drawing for partially illustrating a method for manufacturing the absorbent article 1 according to this embodiment.

Next, a method for manufacturing an absorbent article 1 according to this embodiment is described referring to the accompanying drawings. FIG. 2 is a drawing for partially illustrating the method for manufacturing an absorbent article 1 according to this embodiment.

As shown in FIG. 2, the method for manufacturing an absorbent article 1 includes at least a waistline portion forming step S1, a crotch portion transferring step S2, a leg-surrounding portion forming step S3, a folding step S4, a joining step S5 and a cutting step S6.

In the waistline portion forming step S1, gathers 50 are placed between a web 6A and a web 6B so as to form a pair of webs 61 and 62 respectively corresponding to the pair of waistline portions 10.

Provided with the leg gather 50, the webs 61 and 62 (webs 6A and 6B) can contract (extend) in a cross direction CD orthogonal to the machine direction MD along a flow direction of a manufacturing process for the absorbent article 1. Moreover, the webs 61 and 62 pass a center in the machine direction MD and are asymmetrical each other with reference to a center line CL along the machine direction MD.

In the crotch portion transferring step S2 following (downstream of) the waistline portion forming step S1, a crotch portion member 20A to be fitted to the crotch portion 20 is transferred (disposed) between the pair of webs 61 and 62 at a predetermined intervals along the machine direction MD. The crotch portion member 20A includes the topsheet 2, the backsheet 3, the absorber 4 and the like.

In the leg-surrounding portion forming step S3 following (downstream of) the crotch portion transferring step S2, a portion of the backsheet 3 made into the webs 61 and 62 (webs 6A and 6B) and the crotch portion member 20A is cut. An airspace AR is formed by the waistline opening portion to be fitted to one absorbent article 1 and another the waistline opening portion to be fitted to another absorbent article 1 close to the absorbent article 1.

In the folding step S4 (downstream) following the leg-surrounding portion forming step S3, a pair of webs 61 and 62 is folded in the cross direction CD with reference to a folding line on the crotch member 20A parallel with the machine direction MD. Specifically, a side edge 10A of one web 61 and a side edge 10B of the other web 62 are folded into two by aligning with each other in a predetermined positional relationship with reference to the folding line, whereby an intermediate web 6 is obtained. At this time, an airspace AR becomes of a semicircle-like shape in a plan view of the folded intermediate web 6.

According to this embodiment, the folding line is the center line CL which passes a center of the intermediate web 6 in the cross direction CD and extends toward the machine direction MD. Moreover, the folding line may not necessarily be the center line CL, but may be shifted from the center line CL toward the side edge 1 OA or the side edge 20A.

In the joining step S5 following (downstream of) the folding step S4, a web joint apparatus 200 (refer to FIG. 6) described later performs joining on a joint region 40A to be formed into the joint portion 30 where the pair of waistline portions 10 are joined together. The joint regions 40A are formed respectively on both sides of an imaginary line SL indicating an intended cutting position extending in the cross direction CD of the intermediate web 6.

In the joint step S5, when joining is performed on the joint region 40A by the ultrasonic horn and the anvil roll 222, a crotch hold bar 240 holds the intermediate web 6 while stretching the intermediate web 6 in a direction where the crotch member 20A gets away from the waistline portions 10 and along the cross direction CD.

In the cutting step S6 following (downstream of) the joining step S5, intermediate webs 6 joined at the joint area 40A are cut at predetermined intervals in the machine direction MD, that is, along the imaginary line SL, whereby individual absorbent articles 1 are manufactured.

Figure 3:
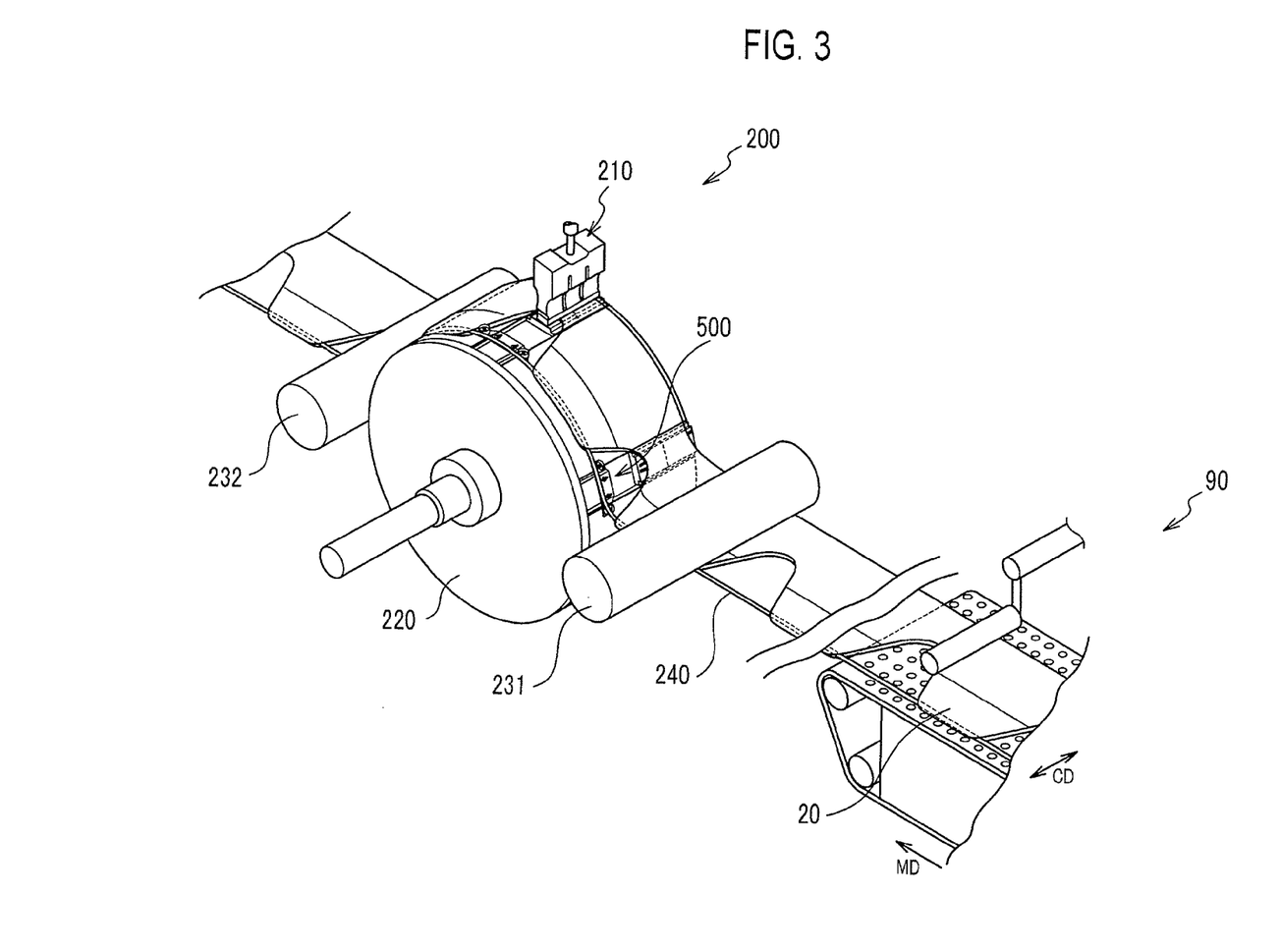
FIG. 3 is a perspective view showing a web joint apparatus 200 according to this embodiment.

Next, a configuration of the web joint apparatus 200 according to this embodiment is described referring to the accompanying drawings. FIG. 3 is a perspective view showing a web joint apparatus 200 according to this embodiment.

As shown in FIG. 3, the web joint apparatus 200 is located downstream of the folding apparatus 90 (folding mechanism) which folds the webs 61 and 62 in the cross direction CD with reference to the folding line in the folding step S4. The web joint apparatus 200 forms the intermediate web 6 and the joint portion 30 by joining the joint region 40A corresponding to the joint portion 30. The web joint apparatus 200 includes an ultrasonic mechanism 210 (joint mechanism), a rotary drum 220 (anvil mechanism), guide rolls, a crotch hold bar 240 (hold mechanism) and a restricting unit 500.

The ultrasonic mechanism 210 applies ultrasonic vibration to the joint region 40A of the intermediate web 6 by holding the joint region 40A in coordination with an anvil roll 222 in the rotary drum 220 described later. The ultrasonic mechanism 210 includes at least an ultrasonic horn which joins the joint region 40A to be formed into the joint portion 30. The ultrasonic horn applies ultrasonic vibration oscillated from an ultrasonic vibrator (not shown) to the joint region 40A by contacting the anvil roll 222 beyond the intermediate web 6 so as to join the joint region 40A.

The rotary drum 220 conveys the intermediate web 6 toward the machine direction MD while supporting the intermediate web 6. The rotary drum 220 is provided with multiple anvil rolls 222 fixed at concave portions 221 (refer to FIG. 4)

recessed from an outer peripheral surface of the rotary drum 220. The anvil rolls 222 face the ultrasonic horn beyond the intermediate web 6, and the multiple anvil rolls (for example, five) are provided on an outer peripheral surface of the rotary drum 220 at a predetermined interval in the machine direction MD. The anvil rolls 222 project externally from the rotary drum 220.

A guide roll supports the intermediate web 6 and the crotch hold bar 240 so that the intermediate web 6 and the crotch hold bar 240 are located along the outer peripheral surface of the rotary drum 220. The guide roll opposes the rotary drum 220 beyond the intermediate web 6. The guide roll includes an upstream roll 231 located upstream of the rotary drum 220 and a downstream roll 232 located downstream of the rotary drum 220.

The crotch hold bar 240 holds the intermediate web 6 in a conveyable manner in a direction where the crotch member 20A gets away from the waistline portions 10 and with the intermediate web 6 stretched along the cross direction CD. The crotch hold bar 240 holds the stretched intermediate web 6 so as not to allow contraction of the intermediate web 6.

Displacement of the crotch hold bar 240 is restricted (held) by the restricting unit 500 described later. The crotch hold bar 240 stretches the folded intermediate web 6 from the inside of the crotch member 20A thereof.

The crotch hold bar 240 is provided at a position where the intermediate web 6 can be stretched from the inside of the crotch member 20A, which guides the intermediate web 6 slidably. The inside of the crotch member 20A represents a section between a part of the top sheet 2 on one of the waistline portion 10 and a part of the top sheet 2 on another one of the waistline portion 10, when a pair of the webs 61 and 62 is folded into two.

Such crotch hold bar 240 is provided at least over an area from the folding apparatus 90 to a location where joining is performed on the joint region 40A by the ultrasonic horn and the anvil rolls 222. According to this embodiment, the crotch hold bar 240 exists over an area between a location where folding of a pair of the webs 61 and 62 is finished by the folding step S4 and a location of the web joint apparatus 200 used in the joint step S5.

Specifically, the crotch hold bar 240 is disposed along a portion of the outer peripheral surface of the rotary drum 220. In an axial view of the rotary drum 220, the intermediate web 6 and the crotch hold bar 240 pass the outer peripheral surface of the rotary drum 220 located upstream.

According to this embodiment, the crotch hold bar 240 is configured by extension of the folding guide bar constituting the folding apparatus 90 used in the folding step S4. Meanwhile, the folding guide bar extends on the folding line along the machine direction MD so as to press a base point where one web 61 and another web 62 are folded onto each other.

The crotch hold bar 240 has a rod-like member extending along the machine direction MD. Cross section of the crotch hold bar 240 in a lateral direction has a circular shape. The crotch hold bar 240 is formed with a metal material and coated with a coating material made of fluorine resin (for example, a tube made of the polytetrafluoroethylene).

Figure 4:
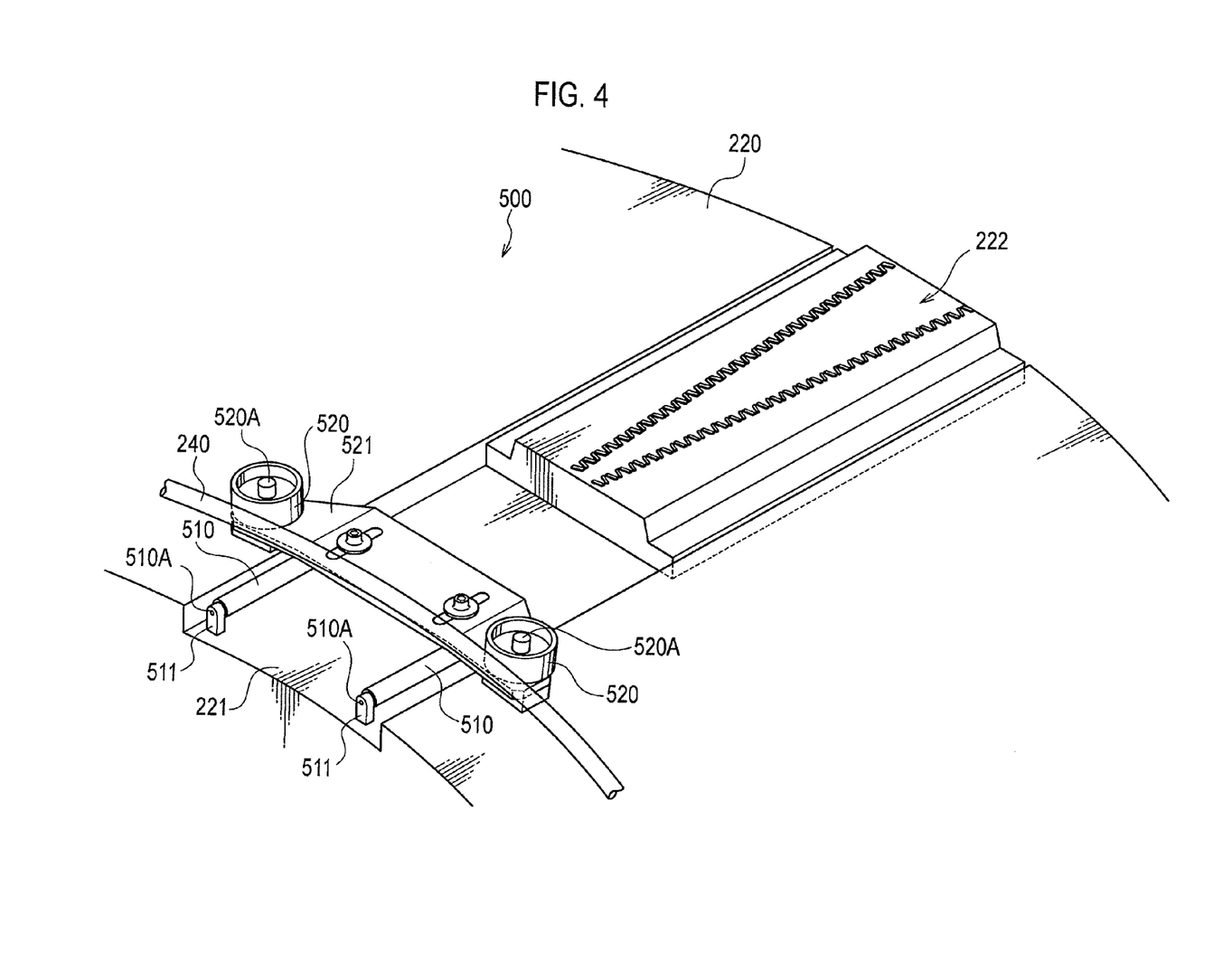
FIG. 4 is a perspective view showing the vicinity of a restricting unit 500 according to this embodiment.
Figure 5:
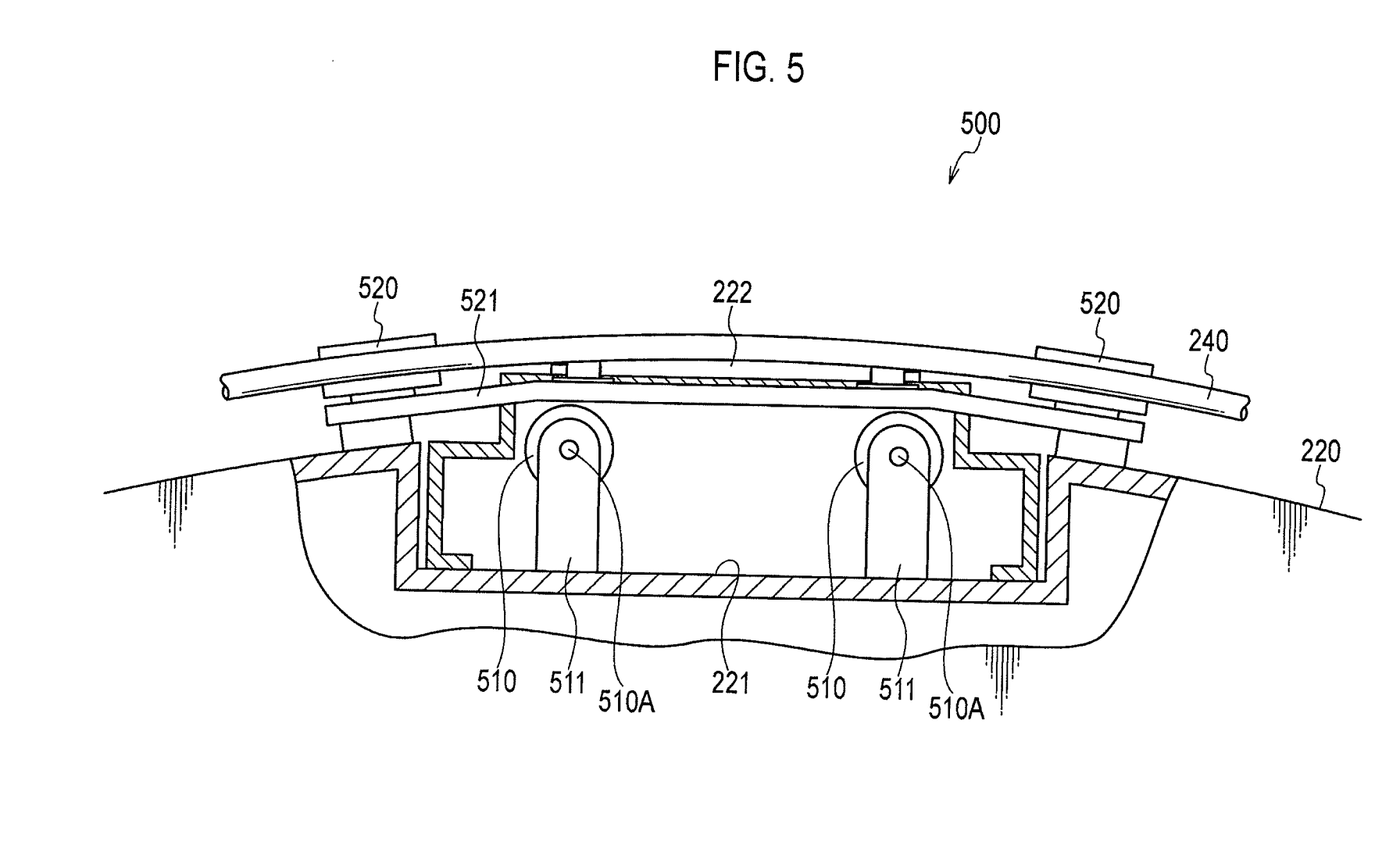
FIG. 5 is a cross sectional view showing a portion of a rotary drum 220 according to this embodiment.

Next, a configuration of the restricting unit 500 according to this embodiment is described referring to a drawing. FIG. 4 is a perspective view showing the vicinity of the restricting unit 500 according to this embodiment. FIG. 5 is a cross sectional view showing a portion of the rotary drum 220 according to this embodiment.

As shown in FIG. 4 and FIG. 5, the restricting unit 500 restricts the displacement of the crotch hold bar 240 described later. The restricting unit 500 is provided on a portion of the outer peripheral surface of the rotary drum 220 and rotates together with the rotary drum 220. The multiple (for example, five) restricting units are provided in a circumferential direction of rotary drum 220 at same locations as the anvil rolls 222.

When the intermediate web 6 passes the outer peripheral surface of the rotary drum 220, the restricting unit 500 rotates at the position of the airspace AR disposed on the intermediate web 6 being conveyed (refer to FIG. 3). Specifically, the restricting unit 500 is located within an area from the crotch hold bar 240 to the waistline portions 10 of the intermediate web 6. In particular, the restricting unit 500 is preferably provided close to a larger side in a semicircle-like space formed by the intermediate web 6 in a plan view of the intermediate web 6.

The restricting unit 500 includes a roller capable of rotating in the machine direction MD of the intermediate web 6 by coming into contact with the crotch hold bar 240. Specifically, the restricting unit 500 includes at least multiple first rollers and multiple second rollers 520.

A first roller 510 reduces friction between the rotary drum 220 and the crotch hold bar 240. The first roller 510 includes a vertical restriction portion restricting a displacement of the crotch hold bar 240 along a vertical direction. The first roller 510 is supported by a frame 511 fixed to concave portions 221 of the rotary drum 220. The first roller 510 includes an axis 510A same as a shaft center of the rotary drum 220. The first roller 510 has a vertically long shape in the width direction of the rotary drum 220. The first roller 510 projects beyond the outer peripheral surface of the rotary drum 220 (refer to FIG. 3). The first roller 510 rotates in contact with the rotary drum 220 at the crotch hold bar 240 when the rotary drum 220 rotates.

The second roller 520 restricts the displacement of the crotch hold bar 240 toward a side closer to the waistline portions 10 of the intermediate web 6. The second roller 520 constitutes a cross restricting unit which districts the displacement of the crotch hold bar 240 in the cross direction CD. A second roller 520 restricts a displacement of the crotch hold bar 240 toward a side closer to the waistline portions 10 of the intermediate web 6, that is, a displacement along the cross direction CD. The second roller 520 is supported by a frame 521 fixed to the outer peripheral surface of the rotary drum 220. The second roller 520 includes an axis 520A along a direction crossing the shaft center of the rotary drum 220 at right angle (in a radial direction of the rotary drum 220). Width of the second roller 520 is set to be larger than the diameter of the crotch hold bar 240. The second roller 520 rotates in contact with the waistline portions 10 of the intermediate web 6 at the crotch hold bar 240.

According to the embodiment described above, the crotch hold bar 240 holds the intermediate web 6 in a conveyable manner while stretching the intermediate web 6 in a direction in which the crotch member 20A gets away from the waistline portions 10 when joining is performed on the intermediate web 6 by the ultrasonic horn and the anvil rolls 222. Thereby, the crotch hold bar 240 can suppress contraction of the intermediate web 6 (in particular, a vicinity of leg-surrounding openings) in the cross direction CD even when a gather 50 is provided around the peripheral edge of leg-surrounding openings. Thereby, even when joining is performed on the intermediate web 6, that is, even when the intermediate web 6 is pressed, a defect such as a crease is unlikely to occur at the joint portion 30 of a pair of the waistline portions 10, and thereby manufacture defect of the absorbent article can be prevented more surely.

Furthermore, even when conveyed along outer peripheral circumference of the rotary drum 220, the intermediate web 6 does not curls up in a direction where the crotch member 20A gets away from the rotary drum 220 by centrifugal force, that is, in the normal direction. Consequently, manufacture defect of the absorbent article can be prevented more surely and failure of the web joint apparatus 200 can be prevented.

According to this embodiment, the crotch hold bar 240 is provided at least over an area from the folding apparatus 90 to a location where joining is performed on the joint region 40A by the ultrasonic horn and the anvil rolls 222. That is, the crotch hold bar 240 exists over an area between a location where folding of a pair of the webs 61 and 62 is finished in the folding step S4, and a location of the web joint apparatus 200 used in the joining step S5. Thereby, the crotch hold bar 240 can convey and hand over the intermediate web 6 to the web joint apparatus 200 with the intermediate web 6 not contracting in the cross direction CD. As a result, occurrence of a defect such as a crease on the intermediate web 6 can be prevented more surely.

According to this embodiment, the crotch hold bar 240 stretches the folded intermediate web 6 from the inside of the crotch member 20A thereof. For example, when the intermediate web 6 is stretched by a belt conveyor holding the intermediate web 6 from the outside of the crotch member 20A, a defect such as crease may occur at the outside of the crotch member 20A (on the side of backsheet 3) between the outside of the crotch member 20A and the belt conveyor. However, if the crotch hold bar 240 stretches the intermediate web 6 from the inside of the crotch member 20A, the crotch hold bar 240 does not contact the outside of the crotch member 20A and a contact area between the crotch hold bar 240 and the intermediate web 6 becomes smaller, whereby a defect such as crease is unlikely to occur on the outside of the crotch member 20A.

According to this embodiment, the crotch hold bar 240 includes a rod-like member extending in the machine direction MD. For example, compared with a case where the intermediate web 6 is stretched by a belt conveyor holding the intermediate web 6 from outside of the crotch member 20A, the crotch hold bar 240 can be installed on the web joint apparatus 200 at low cost and easily and occurrence of a defect such as a crease on the intermediate web 6 can be prevented more surely.

According to this embodiment, the web joint apparatus 200 includes the restricting unit 500 which restricts the displacement of the crotch hold bar 240. The restricting unit 500 is located at an airspace AR disposed on the intermediate web 6 by the waistline portions 10 when the intermediate web 6 passes the outer peripheral surface of the rotary drum 220. Thereby, the restricting unit 500 can restrict a displacement of the crotch hold bar 240 even when the crotch hold bar 240 is forced to displace toward the waistline portions 10 due to stress contracting the intermediate web 6. Thereby, the crotch hold bar 240 can suppress contraction of the intermediate web 6 surely and occurrence of a defect such a crease on the intermediate web 6 can be prevented more surely.

According to this embodiment, the restricting unit 500 includes the first roller 510 which restricts a displacement of the crotch hold bar 240 in the vertical direction. Thereby, the crotch hold bar 240 contacts the first roller 510 without directly contacting an outer peripheral surface of the rotary drum 220. Consequently, friction between the rotating rotary drum 220 and the not-rotating crotch hold bar 240 is reduced. Thus, occurrence of a defect such as crease on the intermediate web 6 can be prevented more steadily while the crotch hold bar 240 is prevented from interfering rotation of the rotary drum 220.

According to this embodiment, the restricting unit 500 includes the second roller 520 which restricts a displacement of the crotch hold bar 240 in the cross direction CD by coming into contact with the crotch hold bar 240. Thereby, the crotch hold bar 240 contacts the second roller 520 even when the crotch hold bar 240 is forced to displace toward the waistline portions 10 of the intermediate web 6 due to a contraction stress of the intermediate web 6 in the cross direction CD. Consequently, the intermediate web 6 stretched along the cross direction CD by the crotch hold bar 240 can be held surely, and thereby a defect such as a crease on the intermediate web 6 can be prevented more surely.

According to this embodiment, when the intermediate web 6 passes the outer peripheral surface of the rotary drum 220, the restricting unit 500 rotates, together with the rotary drum 220, at the position of the airspace AR formed by the intermediate web 6. Consequently, the restricting unit 500 does not come into contact with the intermediate web 6, and thereby occurrence of a defect such as a crease on the intermediate web 6 can be prevented even more steadily.

According to this embodiment, the restricting unit 500 includes rollers (the first roller 510 and the second roller 520) capable of rotating in the machine direction MD of the intermediate web 6 by coming into contact with the crotch hold bar 240. Thereby, the crotch hold bar 240 can prevent contraction of the web 61 in the cross direction when the crotch hold bar 240 is disposed at a portion (above) the outer peripheral surface of the rotary drum 220.

According to this embodiment, cross section of the crotch hold bar 240 in a lateral direction has a circular shape. The crotch hold bar 240 is formed with a metal material and coated with a coating material made of fluorine resin. Thereby, inside of the crotch portion 20 on the web 61 is likely to slide on the crotch hold bar 240, whereby, compared with the pair of waistline portions 10, conveyance delay of the crotch portion 20 can be prevented, and occurrence of a defect such as a crease and twist on the crotch portion 20 can be prevented.

Modified Embodiment

Figure 6:
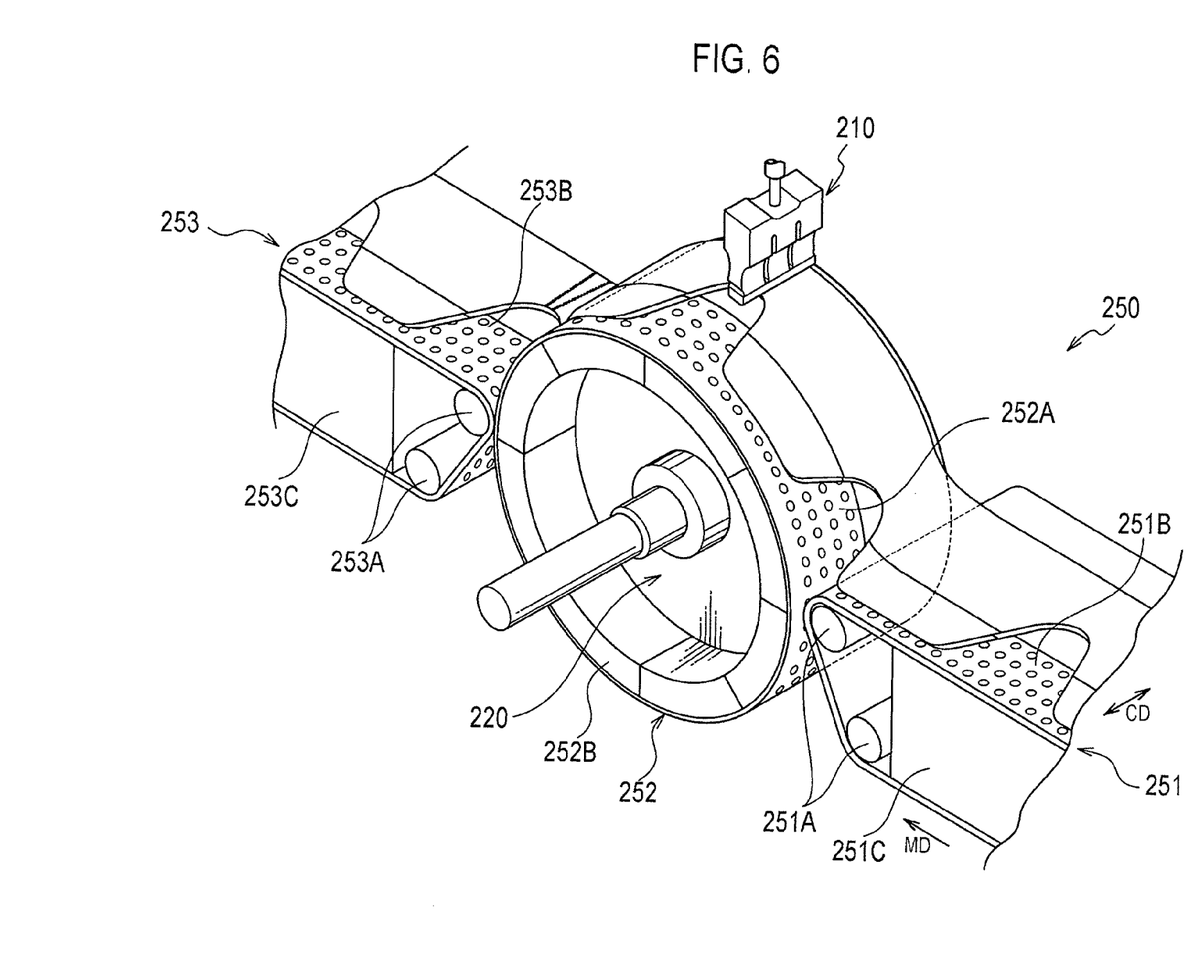
FIG. 6 is a perspective view showing a portion of a hold mechanism according to a modified embodiment (1).

Next, a modified hold mechanism according to the embodiment described above is described referring to a drawing. FIG. 6 is a perspective view showing a portion of the hold mechanism according to a modified embodiment. Members same as those of the hold mechanism according to the embodiment described above are denoted with same signs, and description is focused on differences.

According to the embodiment described above, the crotch hold bar 240 extending along the machine direction MD serves as a hold mechanism, whereas, according to the modified embodiment, a conveyor 250 comprising a first conveyor 251, a second conveyor 252 and a third conveyor 253 serves as a hold mechanism.

The first conveyor 251 is configured to rotate around multiple rollers 251A and multiple rollers 251A and also suction external air via a conveyor belt 251B with multiple holes disposed thereon for air passage, a driving means (not shown) which makes the conveyor belt rotate around the multiple rollers 251A, and holes disposed on the conveyor belt 251. The first conveyor 251 includes a suction mechanism 251C configured to attract the intermediate web 6 located on the conveyor belt 251B.

The second conveyor 252 is capable of rotating with a rotary drum 220 disposed along outer peripheral surface of the rotary drum 220 and also suctioning external air via a rotary belt 252A with multiple holes disposed thereon for air passage and holes disposed on the rotary belt 252A. The second conveyor belt includes a suction mechanism 252B configured to attract the intermediate web 6 located on the rotary belt 252A.

Figure 7:
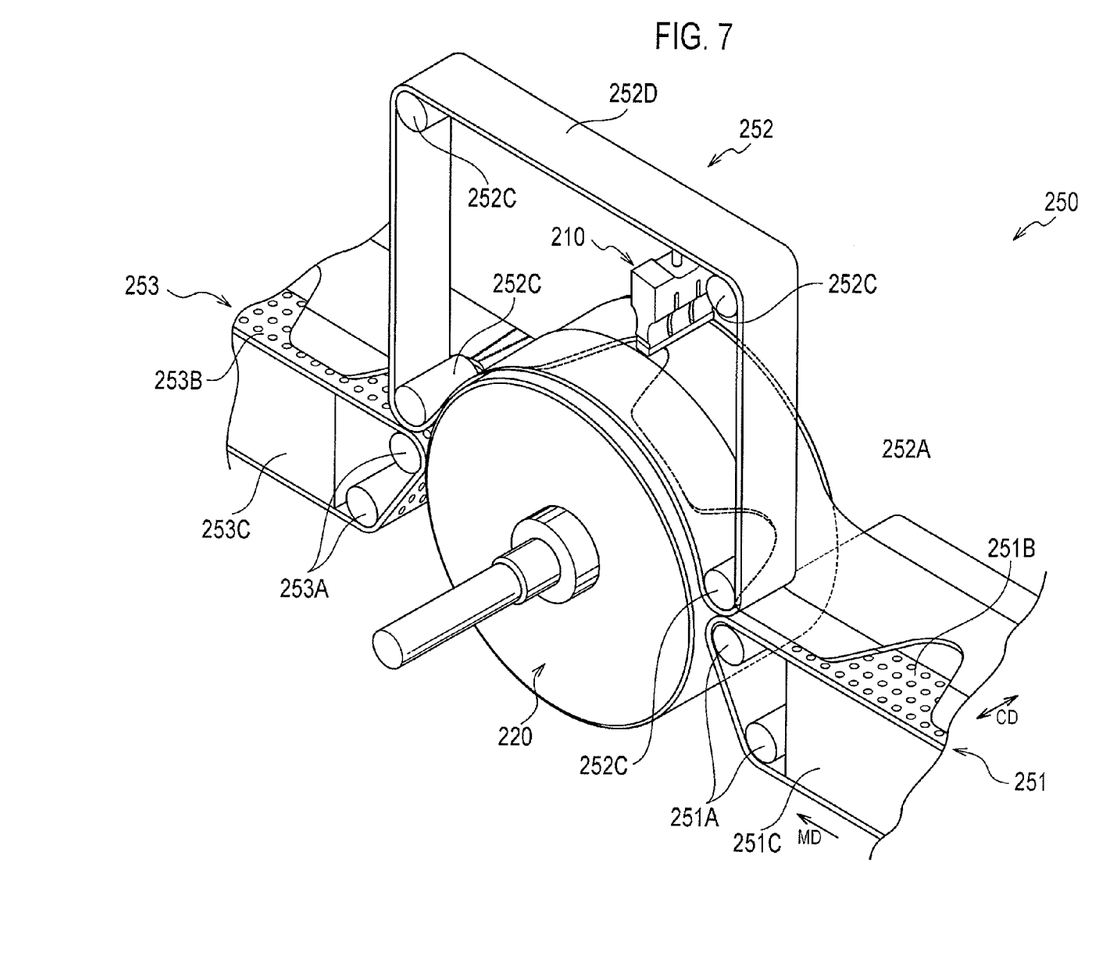
FIG. 7 is a perspective view showing a portion of a hold mechanism according to a modified embodiment (2).

Meanwhile, the second conveyor 252 does not need to include the rotary belt 252A and the suction mechanism 252B. For example, as shown in FIG. 7, the second conveyor 252 may include multiple rollers 252C and a press belt 252D which rotates around multiple rollers 252C. In an axial view of the rotary drum 220, the press belt 252D presses the intermediate web 6 onto the outer peripheral surface of the rotary drum 220 located upstream.

The third conveyor 253 includes, similarly with the first conveyor 251, multiple rollers 253A, a driving means (not shown) and a suction mechanism 253C.

According to the modified embodiment described above, the intermediate web 6 being stretched along a direction where the crotch portion 20 gets away from the waistline portions 10 can be held in a conveyable manner without using the crotch hold bar 240 described in the embodiment.

Other Embodiments

As described above, details of the present invention are disclosed through various preferable embodiments. However, it should not be understood that description and drawings constituting part of this disclosure limits the present invention. It will be apparent to those skilled in the art that various alternative embodiments, modifications and operational techniques can be made.

For example, an embodiment according to the present invention can be modified. Specifically, although the absorbent article 1 is described as being formed in combination of a pair of waistline portions 10 and crotch portion 20 (so-called three-piece type), it is not limited thereto. Alternatively, the absorbent article 1 may be formed by integrating a pair of waistline portions 10 and crotch portion 20 all together (so-called one-piece type). Moreover, configurations of the absorbent article 1 are not limited to those described in the embodiments, but may be set up appropriately in accordance with any intended use.

Furthermore, although the absorbent article 1 is described as being a pants-type disposable diaper, it is not limited thereto. Alternatively, it may be an article manufactured using the folding step S4 (for example, an open-type diaper or napkin). Moreover, configurations of the absorbent article 1 are not limited to those described on the embodiments, but may be selected suitably according to an intended purpose.

Furthermore, although the webs 61 and 62 are described as having property likely to contract (expand) in the cross direction CD by the waist gather 50, it is not limited thereto. Alternatively, the webs 61 and 62 may be made of a sheet having a self-contracting property.

Furthermore, although the webs 61 and 62 are described as being asymmetrical based on the central line CL, it is not limited to this. Alternatively, the webs 61 and 62 may be asymmetrical with respect to the center line CL.

The method for manufacturing the absorbent article 1 is not limited to those described on the embodiments. Order of steps may be changed (for example, the leg-surrounding portion forming step S3 may be included in the cutting step S6) as far as the absorbent article 1 can be manufactured.

Moreover, the web joint apparatus 200 is not limited to the configuration according to the foregoing embodiment, and may be configured to perform heating treatment, for example.

Furthermore, although the restricting unit 500 is described as being a roller rotatable in the machine direction MD of the intermediate web 6, it is not limited thereto. Instead of the roller, the restricting unit 500 may be a member which is capable of suppressing the crotch hold bar 240 (for example, a projection projecting from an outer peripheral surface of the rotary drum 220).

Furthermore, although the restricting unit 500 is described as being located within an area from the crotch hold bar 240 to the waistline portions 10 of the intermediate web 6, the location is not limited thereto. The restricting unit 500 may be provided within an area from the crotch hold bar 240 to the waistline portions 10 of the intermediate web 6, and within an area from the crotch hold bar 240 to a side of the rotary drum 220 opposite to the waistline portions.

As described above, the present invention obviously includes other various embodiments contained herein. Thus, technical scope of the present invention will be determined by specific invented items according to the scope of claims appropriate from above descriptions.

Note that, the entire content of Japanese Patent Application No. 2009-180201 (filed on Jul. 31, 2009) is incorporated herein by reference.

INDUSTRIAL APPLICABILITY

The present invention can provide a web joint apparatus and a web joint method which can surely prevent a crotch portion from bending in the normal direction of an anvil roll in joining webs folded into two and also can prevent manufacture defects of an absorbent article more surely.

The invention claimed is:

1. A web joint apparatus for a web for absorbent articles, the web being folded into two in a cross direction orthogonal to a machine direction with reference to a folding line parallel with the machine direction on crotch portions in the web,
   the web including:
      paired waistline portions which are continuous in the machine direction along a flow direction of a manufacturing process for the absorbent articles; and
      the crotch portions which are discontinuous in the machine direction and located between the paired waistline portions,
   the web joint apparatus comprising:
      a joint mechanism configured to join the paired waistline portions;
      an anvil mechanism facing the joint mechanism and configured to join the web between the anvil mechanism and the joint mechanism; and
      a hold mechanism configured to hold the web while stretching the web in a direction in which the crotch portions move away from the waistline portions, when the paired waistline portions are joined by the joint mechanism and the anvil mechanism,
   wherein
      the hold mechanism includes a rod member extending in the machine direction, and
      the anvil mechanism includes a restricting unit configured to restrict a displacement of the rod member.

2. The web joint apparatus according to claim 1, further comprising:
   a folding mechanism provided upstream of the joint mechanism in the machine direction, and configured to fold the web in the cross direction orthogonal to the machine direction with reference to the folding line, wherein the hold mechanism is provided at least over an area from the folding mechanism to a location where the paired waistline portions are joined by the joint mechanism and the anvil mechanism.

3. The web joint apparatus according to claim 1, wherein the hold mechanism is configured to stretch the web from an inside of the crotch portions of the folded web.

4. The web joint mechanism according to claim 1, wherein the restricting unit includes a vertical restricting portion configured to come into contact with the rod member to restrict a displacement of the rod member in a vertical direction.

5. The web joint mechanism according to claim 1, wherein the restricting unit includes a cross restricting portion configured to come into contact with the rod member to restrict a displacement of the rod member in the cross direction.

6. The web joint mechanism according to claim 1, wherein the restricting unit is located at an airspace formed by neighboring pairs of the waistline portions on the web when the web passes an outer peripheral circumference of a rotary drum of the anvil mechanism.

7. The web joint mechanism according to claim 1, wherein the restricting unit includes a roller rotatable in a conveyance direction of the web.

8. A web joint method of joining paired waistline portions in a web for absorbent articles, the web being folded into two in a cross direction orthogonal to a machine direction with reference to a folding line parallel with the machine direction on crotch portions in the web, the web including:
   the paired waistline portions which are continuous in the machine direction along a flow direction of a manufacturing process for the absorbent articles; and
   the crotch portions which are discontinuous in the machine direction and located between the paired waistline portions, the web joint method comprising:
   joining the paired waistline portions together by using a joint mechanism and an anvil mechanism, the joint mechanism configured to join the paired waistline portions, the anvil mechanism facing the joint mechanism and configured to join the web between the anvil mechanism and the joint mechanism, wherein in said joining, a hold mechanism holds the web while stretching the web in a direction in which the crotch portions move away from the waistline portions, when the paired waistline portions are joined by the joint mechanism and the anvil mechanism, the hold mechanism includes a rod member extending in the machine direction, and the anvil mechanism includes a restricting unit that restricts a displacement of the rod member.

\* \* \* \* \*